US012758694B2

(12) United States Patent
Ravikumar et al.

(10) Patent No.: US 12,758,694 B2
(45) Date of Patent: Oct. 13, 2026

(54) DIALYSIS SYSTEM HAVING PUMP REVERSING DISINFECTION

(71) Applicants: Vantive US Healthcare LLC, Deerfield, IL (US); Vantive Health GMBH, Glattpark (CH)

(72) Inventors: Hemanth Hiriyur Ravikumar, Bengaluru (IN); Sachin Sunkad, Bangalore (IN); Akhilesh Sham Sundar Vibhute, Bangalore (IN)

(73) Assignees: Vantive US Healthcare LLC, Deerfield, IL (US); Vantive Health GMBH, Glattpark (CH)

( * ) Notice: Subject to any disclaimer, the term of this patent is extended or adjusted under 35 U.S.C. 154(b) by 415 days.

(21) Appl. No.: 18/367,703

(22) Filed: Sep. 13, 2023

(65) Prior Publication Data

US 2024/0082469 A1 Mar. 14, 2024

(51) Int. Cl.
*A61M 1/28* (2006.01)
*A61M 1/16* (2006.01)

(52) U.S. Cl.
CPC .......... *A61M 1/168* (2013.01); *A61M 1/1686* (2013.01); *A61M 1/28* (2013.01); *A61M 1/282* (2014.02); *A61M 2205/3368* (2013.01)

(58) Field of Classification Search
CPC ...... A61M 1/168; A61M 1/1686; A61M 1/28; A61M 1/282; A61M 2205/3368
See application file for complete search history.

(56) References Cited

U.S. PATENT DOCUMENTS

| | | | | |
|---|---|---|---|---|
| 2020/0129927 A1* | 4/2020 | Sendelius | ............ | B01D 65/027 |
| 2022/0280703 A1* | 9/2022 | Bonczar | ................ | A61M 1/155 |

* cited by examiner

*Primary Examiner* — John Kim
(74) *Attorney, Agent, or Firm* — K&L Gates LLP

(57) ABSTRACT

A peritoneal dialysis ("PD") system includes a housing, a PD fluid pump housed by the housing, an inline heater in fluid communication with the PD fluid pump, a temperature sensor, and a control unit. The PD fluid pump and the inline heater are under control of the control unit, which receives a temperature signal from the temperature sensor. The control unit, in one embodiment, is configured to perform a heat disinfection sequence in which the control unit causes the PD fluid pump to pump disinfection fluid in a forward direction, while the inline heater heats the disinfection fluid, and in a reverse direction after the temperature signal indicates that a temperature of the disinfection fluid has fallen to or has fallen below a minimum disinfection temperature.

20 Claims, 7 Drawing Sheets

DIALYSIS SYSTEM HAVING PUMP REVERSING DISINFECTION

PRIORITY CLAIM

This application claims priority to and the benefit of Indian Provisional Patent Application Ser. No. 202241052405, filed on Sep. 14, 2022, the entire disclosure of which is hereby incorporated by reference.

BACKGROUND

The present disclosure relates generally to medical fluid treatments, and in particular to dialysis fluid treatments that require the pumping of patient-injectable fluids.

Due to various causes, a person's renal system can fail. Renal failure produces several physiological derangements. It is no longer possible to balance water and minerals or to excrete daily metabolic load. Toxic end products of metabolism, such as, urea, creatinine, uric acid and others, may accumulate in a patient's blood and tissue.

Reduced kidney function and, above all, kidney failure is treated with dialysis. Dialysis removes waste, toxins, and excess water from the body that normal functioning kidneys would otherwise remove. Dialysis treatment for replacement of kidney functions is critical to many people because the treatment is lifesaving.

One type of kidney failure therapy is Hemodialysis ("HD"), which in general uses diffusion to remove waste products from a patient's blood. A diffusive gradient occurs across the semi-permeable dialyzer between the blood and an electrolyte solution called dialysate or dialysis fluid to cause diffusion.

Hemofiltration ("HF") is an alternative renal replacement therapy that relies on a convective transport of toxins from the patient's blood. HF is accomplished by adding substitution or replacement fluid to the extracorporeal circuit during treatment. The substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is a treatment modality that combines convective and diffusive clearances. HDF uses dialysis fluid flowing through a dialyzer, similar to standard hemodialysis, to provide diffusive clearance. In addition, substitution solution is provided directly to the extracorporeal circuit, providing convective clearance.

Most HD, HF, and HDF treatments occur in centers. A trend towards home hemodialysis ("HHD") exists today in part because HHD can be performed daily, offering therapeutic benefits over in-center hemodialysis treatments, which occur typically bi- or tri-weekly. Studies have shown that more frequent treatments remove more toxins and waste products and render less interdialytic fluid overload than a patient receiving less frequent but perhaps longer treatments. A patient receiving more frequent treatments does not experience as much of a down cycle (swings in fluids and toxins) as does an in-center patient, who has built-up two or three days' worth of toxins prior to a treatment. In certain areas, the closest dialysis center can be many miles from the patient's home, causing door-to-door treatment time to consume a large portion of the day. Treatments in centers close to the patient's home may also consume a large portion of the patient's day. HHD can take place overnight or during the day while the patient relaxes, works or is otherwise productive.

Another type of kidney failure therapy is peritoneal dialysis ("PD"), which infuses a dialysis solution, also called dialysis fluid, into a patient's peritoneal chamber via a catheter. The dialysis fluid is in contact with the peritoneal membrane in the patient's peritoneal chamber. Waste, toxins, and excess water pass from the patient's bloodstream, through the capillaries in the peritoneal membrane, and into the dialysis fluid due to diffusion and osmosis, i.e., an osmotic gradient occurs across the membrane. An osmotic agent in the PD dialysis fluid provides the osmotic gradient. Used or spent dialysis fluid is drained from the patient, removing waste, toxins, and excess water from the patient. This cycle is repeated, e.g., multiple times.

There are various types of peritoneal dialysis therapies, including continuous ambulatory peritoneal dialysis ("CAPD"), automated peritoneal dialysis ("APD"), tidal flow dialysis and continuous flow peritoneal dialysis ("CFPD"). CAPD is a manual dialysis treatment. Here, the patient manually connects an implanted catheter to a drain to allow used or spent dialysis fluid to drain from the peritoneal chamber. The patient then switches fluid communication so that the patient catheter communicates with a bag of fresh dialysis fluid to infuse the fresh dialysis fluid through the catheter and into the patient. The patient disconnects the catheter from the fresh dialysis fluid bag and allows the dialysis fluid to dwell within the peritoneal chamber, wherein the transfer of waste, toxins and excess water takes place. After a dwell period, the patient repeats the manual dialysis procedure, for example, four times per day. Manual peritoneal dialysis requires a significant amount of time and effort from the patient, leaving ample room for improvement.

Automated peritoneal dialysis ("APD") is similar to CAPD in that the dialysis treatment includes drain, fill and dwell cycles. Automated PD machines, however, perform the cycles automatically, typically while the patient sleeps. The PD machines free patients from having to manually perform the treatment cycles and from having to transport supplies during the day. The PD machines connect fluidly to an implanted catheter, to a source or bag of fresh dialysis fluid and to a fluid drain. The PD machines pump fresh dialysis fluid from a dialysis fluid source, through the catheter and into the patient's peritoneal chamber. The PD machines also allow for the dialysis fluid to dwell within the chamber and for the transfer of waste, toxins and excess water to take place. The source may include multiple liters of dialysis fluid including several solution bags.

The PD machines pump used or spent dialysate from the patient's peritoneal cavity, though the catheter, to drain. As with the manual process, several drain, fill and dwell cycles occur during dialysis. A "last fill" may occur at the end of an APD treatment. The last fill fluid may remain in the peritoneal chamber of the patient until the start of the next treatment, or may be manually emptied at some point during the day.

In any of the above modalities, the automated machine and even manual CAPD operate typically with a disposable set, which is discarded after a single use. Depending on the complexity of the disposable set, the cost of using one set per day may become significant. Also, daily disposables require space for storage, which can become a nuisance for home owners and businesses. Moreover, daily disposable replacement requires daily setup time and effort by the patient or caregiver at home or at a clinic.

For each of the above reasons, it is desirable to provide an APD machine that reduces disposable waste.

SUMMARY

The present disclosure sets forth an automated peritoneal dialysis ("PD") system, which provides one or more PD treatment improvement. The system includes a PD machine or cycler. The PD machine is capable of delivering fresh, heated PD fluid to a patient at, for example, 14 kPa (2.0 psig) or higher. The PD machine is capable of removing used PD fluid or effluent from the patient at, for example, between −5 kPa (−0.73 psig) and −15 kPa (−2.2 psig), such as −9 kPa (−1.3 psig) or higher. Fresh PD fluid may be delivered via a dual lumen patient line to the patient and is first heated to a body fluid temperature, e.g., 37° C. The heated PD fluid is then pumped through a fresh PD fluid lumen of the dual lumen patient line to a disposable filter set, which is connected to the patient's transfer set, which is in turn connected to an indwelling catheter leading into the patient's peritoneal cavity. The disposable filter set communicates fluidly with the fresh and used PD fluid lumens of the dual lumen patient line. The disposable filter set is provided in one embodiment as a last chance filter for the PD machine, which may be heat disinfected between treatments.

The system may include one or more PD fluid container or bag that supplies fresh PD fluid to the PD machine or cycler. The PD machine or cycler may include internal lines having two-way or three-way valves and at least one PD fluid pump for pumping fresh PD fluid from the one or more PD fluid container or bag to a patient and for removing used PD fluid from the patient to a house drain or drain container. One or more flexible PD fluid line leads from the PD machine or cylcer's internal lines to the one or more PD fluid container or bag. The flexible dual lumen patient line mentioned above leads from the PD machine or cylcer's internal lines to the patient. A flexible drain line leads from the PD machine or cylcer's internal lines to the house drain or drain container. The system in one embodiment disinfects all internal lines, the PD fluid lines, and the dual lumen patient line after treatment for reuse in the next treatment. The disinfection may involve heat disinfection using left-over fresh PD fluid.

It is contemplated in one embodiment for the control unit to cause the PD fluid pump and the valves of the system at the beginning of a heat disinfection sequence to move the heated PD fluid in a normal treatment direction. The heated PD fluid splits as needed to flow through the disinfection loop before arriving back at the inline heater. The length of the internal reusable tubing and the flexible reusable flexible PD fluid lines between the outlet of the inline heater and the inlet of inline heater 56 may be ten meters or more. Heat loss occurs over the length of the lines. A potential problem may accordingly occur in which while the PD fluid leaving the inline heater is at a temperature sufficient to produce a desired amount of disinfection, the temperature of PD fluid entering the inline heater is below what is considered a threshold minimum disinfection temperature.

In one example, the control unit under feedback from a downstream temperature sensor energizes the inline heater such that PD fluid exiting the heater is at or about 85° C. 85° C. (185° F.) is in one embodiment a desired output temperature because it is above a recommended minimum disinfection temperature of, e.g., 75° C. (167° F.) and it is below a temperature in which the PD fluid may start to boil. If the temperature of PD fluid reaching the inlet of the inline heater falls below the recommended minimum disinfection temperature of, e.g., 75° C., then corrective action needs to be taken. Corrective measures may include raising the heater outlet temperature, increasing disinfection time or some combination of both. However, raising the heater outlet temperature above 85° C. runs the risk of causing the PD fluid to boil, while increasing disinfection time increases component wear. It should be appreciated that the minimum disinfection temperature may vary, e.g. from 65° C. (149° F.) to 95° C. (203° F.).

The present system and its associated methodology instead solve the potential low temperature problem by programing the control unit to automatically reverse the pumping direction of the PD fluid pump one or more time during the disinfection sequence so that freshly heated PD fluid, e.g., at or about 85° C., is outputted from what is typically the heater inlet of the inline heater. As discussed in detail below, the inline heater is bidirectional in one embodiment. Reversing the pumping direction of the PD fluid pump one or more time during the disinfection sequence causes the freshly heated PD fluid, e.g., to 85° C., to be distributed more evenly. Here, the hotter freshly heated PD fluid mixes with the cooler PD fluid returning to the inline heater, bringing the mixed PD fluid temperature to above the recommended minimum disinfection temperature of, e.g., 75° C. The more even distribution of freshly heated PD fluid helps to eliminate pockets of the closed disinfection loop that may fall below the recommended minimum disinfection temperature. The more even distribution of freshly heated PD fluid also helps to reduce the amount of time needed for the disinfection sequence. For example, the time for the disinfection sequence may be cut roughly in half from two hours to one hour.

In one method for controlling the pump reversing during heat disinfection of the present disclosure, the control unit monitors the output of a temperature sensor located so as to sense the temperature of heated PD fluid reentering the inline heater. In one embodiment, the control unit determines whether the temperature of the PD fluid reentering the inline heater has fallen below a recommended minimum disinfection temperature of, e.g. 75° C., for a designated or threshold amount of time, such as sixty seconds. Including a designated or threshold amount of time in the analysis allows for the PD fluid temperature at the heater inlet to fall below the recommended minimum disinfection temperature for short periods of time, or inadvertently, without overreacting to the temporary temperature drop. It is contemplated to optimize the threshold amount of time to allow for a looser system, e.g., longer than one minute, or for a tighter version of the system, e.g., five to sixty seconds.

When the temperature of the PD fluid reentering the inline heater has fallen below the recommended minimum disinfection temperature for the threshold amount of time, the control unit causes the PD fluid pump to reverse and pump in the opposite direction. It is contemplated for the control unit to control the amount or time that the pumping of the PD fluid pump is reversed in a plurality of different ways. In one way, the control unit causes the PD fluid pump to pump in the reverse direction for a number of pump strokes, e.g., one-hundred pump strokes. In a second way, the control unit causes the PD fluid pump to pump in the reverse direction until a certain temperature is reached at temperature sensor, which is the downstream temperature sensor during reverse pumping. In a third way, the control unit causes the PD fluid pump to pump in the reverse direction until a certain temperature is reached at the downstream temperature sensor during pump reversing, after which a preset number of additional pump strokes are performed in the reverse pumping direction. The control unit causes the above sequence to be repeated until a total disinfection time is reached.

In a second, alternative method the temperature sensor located just upstream of the heater may not be needed, which is advantageous for reducing cost, eliminating a sensor that may need calibration from time to time, and eliminating a part that may need to be replaced. Here, the control unit causes the PD fluid pump to pump in the forward or normal treatment direction for a preset number of pump strokes, e.g., 100 pump strokes. After the preset number of pump strokes in the treatment direction have been completed, the control unit causes the PD fluid pump to automatically reverse and pump in the opposite direction for a preset number of pump strokes, e.g., one-hundred pump strokes. The control unit causes the above sequence to be repeated until a total disinfection time is reached.

The present system and associated methodologies may use a closed loop heater control algorithm or a forward open loop heater control analysis. For closed loop control, the control unit reads the temperature from a downstream temperature sensor. The control unit also stores a target temperature, e.g., at or about 85° C. The control unit calculates an error between the commanded or target temperature and the temperature read from the downstream temperature sensor. The control unit then inputs the calculated error into a closed loop heating algorithm, e.g., PID heating algorithm. An output from the heating algorithm is used by the control unit to determine how much power to deliver to inline heater. The cycle just described is repeated at some processing frequency.

The forward open loop heater control uses an output from an upstream temperature sensor to the control unit. For open loop control, the control unit reads the temperature from the upstream temperature sensor and also stores a target temperature, e.g., 85° C. The control unit also determines (calculates or measures) a current PD fluid flowrate. If a piston pump is used as the PD fluid pump and no flowmeter is provided, the control unit calculates the current flowrate by accumulating known volume pump strokes pumped by the PD fluid pump and dividing the accumulated volume by an amount of time needed to make the pump strokes accumulated. If instead a separate flowmeter is provided, then the control unit measures the flowrate by reading an output from the flowmeter.

The control unit inputs the temperature from the upstream temperature sensor and the determined flowrate into a feed forward heater algorithm. An output from the feed forward heater algorithm (or derivative or correlation thereof) is used by the control unit to determine how much current or power to deliver to inline heater. The cycle just described is repeated at some processing frequency.

In light of the disclosure set forth herein, and without limiting the disclosure in any way, in a first aspect of the present disclosure, which may be combined with any other aspect, or portion thereof, a peritoneal dialysis ("PD") system includes a housing; a PD fluid pump housed by the housing; an inline heater in fluid communication with the PD fluid pump; a temperature sensor; and a control unit, the PD fluid pump and the inline heater under control of the control unit, the control unit receiving a temperature signal from the temperature sensor, the control unit configured to perform a heat disinfection sequence in which the control unit causes the PD fluid pump to pump disinfection fluid in a forward direction, while the inline heater heats the disinfection fluid, and in a reverse direction after the temperature signal indicates that a temperature of the disinfection fluid has fallen to or has fallen below a minimum disinfection temperature.

In a second aspect of the present disclosure, which may be combined with any other aspect, or portion thereof, the control unit is configured to cause the PD fluid pump to pump the disinfection fluid in the reverse direction after the temperature signal indicates, over a designated amount of time, that the temperature of the disinfection fluid has fallen to or has fallen below the minimum disinfection temperature.

In a third aspect of the present disclosure, which may be combined with any other aspect, or portion thereof, the temperature sensor is located upstream of the inline heater when the PD fluid pump is pumping the disinfection fluid in the forward direction.

In a fourth aspect of the present disclosure, which may be combined with any other aspect, or portion thereof, the temperature signal is used as closed loop feedback to the control unit for controlling the inline heater when the PD fluid pump is pumping the disinfection fluid in the reverse direction.

In a fifth aspect of the present disclosure, which may be combined with any other aspect, or portion thereof, the temperature sensor is a first temperature sensor, and which includes a second temperature sensor located downstream of the inline heater when the PD fluid pump is pumping the disinfection fluid in the forward direction, and wherein a temperature signal from the second temperature sensor is used as closed loop feedback to the control unit for controlling the inline heater when the PD fluid pump is pumping the disinfection fluid in the forward direction.

In a sixth aspect of the present disclosure, which may be combined with any other aspect, or portion thereof, the inline heater is controlled such that a temperature of the disinfection fluid exiting the inline heater is about 85° C.

In a seventh aspect of the present disclosure, which may be combined with any other aspect, or portion thereof, the control unit is configured to cause the PD fluid pump to pump the disinfection fluid in the reverse direction for a number of pump strokes.

In an eighth aspect of the present disclosure, which may be combined with any other aspect, or portion thereof, the control unit is configured to cause the PD fluid pump to pump the disinfection fluid in the reverse direction until a certain temperature is reached, as indicated by the temperature sensor.

In a ninth aspect of the present disclosure, which may be combined with any other aspect, or portion thereof, the control unit is configured to cause the PD fluid pump to pump the disinfection fluid in the reverse direction until a certain temperature is reached, as indicated by the temperature sensor, followed by a number of pump strokes in the reverse direction.

In a tenth aspect of the present disclosure, which may be combined with any other aspect, or portion thereof, the heat disinfection sequence is performed using a disinfection loop including a reusable patient line extending from the housing, the reusable patient line including a distal end configured to be connected to a patient line connector provided by the housing; and at least one reusable PD fluid line extending from the housing, the at least one reusable PD fluid line including a distal end configured to be connected to a PD fluid line connector provided by the housing.

In an eleventh aspect of the present disclosure, which may be combined with any other aspect, or portion thereof, at least one of (i) the minimum disinfection temperature is from 65° C. (149° F.) to 95° C. (203° F.) or (ii) the disinfection fluid is PD fluid.

In a twelfth aspect of the present disclosure, which may be combined with any other aspect, or portion thereof, a peritoneal dialysis ("PD") system includes a housing; a PD fluid pump housed by the housing; an inline heater in fluid communication with the PD fluid pump; a temperature sensor; and a control unit, the PD fluid pump and the inline heater under control of the control unit, the control unit receiving a temperature signal from the temperature sensor, the control unit configured to perform a heat disinfection sequence in which the control unit causes the PD fluid pump to pump disinfection fluid in a forward direction, while the inline heater heats the disinfection fluid, and in a reverse direction in which the control unit controls the inline heater using a feed forward algorithm that takes into account the temperature signal and a flowrate of the disinfection fluid.

In a thirteenth aspect of the present disclosure, which may be combined with any other aspect, or portion thereof, the temperature signal provides a heater inlet temperature, and wherein the feed forward algorithm subtracts the inlet temperature from a target temperature.

In a fourteenth aspect of the present disclosure, which may be combined with any other aspect, or portion thereof, the flowrate of the disinfection fluid is calculated by the control unit by accumulating known pump volumes pumped by the PD fluid pump.

In a fifteenth aspect of the present disclosure, which may be combined with any other aspect, or portion thereof, the PD system which includes a flowmeter in fluid communication with the PD fluid pump, and wherein the flowrate of the disinfection fluid is measured by the flowmeter.

In a sixteenth aspect of the present disclosure, which may be combined with any other aspect, or portion thereof, the feed forward algorithm is structured to calculate an output power=(a target temperature−an inlet temperature obtained from the temperature signal)×(the disinfection fluid flowrate)×(the specific heater of water).

In a seventeenth aspect of the present disclosure, which may be combined with any other aspect, or portion thereof, the target temperature is 85° C.

In an eighteenth aspect of the present disclosure, which may be combined with any other aspect, or portion thereof, the temperature sensor is located downstream of the inline heater when the PD fluid pump is pumping the disinfection fluid in the forward direction, and wherein the temperature signal is used as closed loop feedback to the control unit for controlling the inline heater when the PD fluid pump is pumping the disinfection fluid in the forward direction.

In a nineteenth aspect of the present disclosure, which may be combined with any other aspect, or portion thereof, the control unit is configured to cause (i) the PD fluid pump to pump the disinfection fluid in the forward direction for a number of pump strokes, and (ii) the PD fluid pump to automatically reverse and pump the disinfection fluid in the reverse direction for a number of pump strokes.

In a twentieth aspect of the present disclosure, which may be combined with any other aspect, or portion thereof, the control unit is further configured to repeat (i) and (ii) until a total disinfection time is reached.

In a twenty-first aspect of the present disclosure, which may be combined with any other aspect, or portion thereof, any of the features, functionality and alternatives described in connection with any one or more of FIGS. 1, 2 and 4 to 8 may be combined with any of the features, functionality and alternatives described in connection with any other of FIGS. 1, 2 and 4 to 8.

In light of the above aspects and present disclosure set forth herein, it is an advantage of the present disclosure to provide a dialysis system and method having improved heat disinfection.

It is another advantage of the present disclosure to provide a dialysis system and method having heat disinfection with fewer or no pockets of low temperature disinfection fluid.

It is a further advantage of the present disclosure to provide a PD system and method having reduced disinfection times.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the improvements or advantages listed herein, and it is expressly contemplated to claim individual advantageous embodiments separately. In particular, the system of the present disclosure may have any one or more or all of the drip prevention structure and methodology, PD fluid container emptying structure and methodology and patient connection before drain check structure and methodology described herein. Moreover, it should be noted that the language used in the specification has been selected principally for readability and instructional purposes, and not to limit the scope of the inventive subject matter.

DETAILED DESCRIPTION

System Overview

Figure 1:
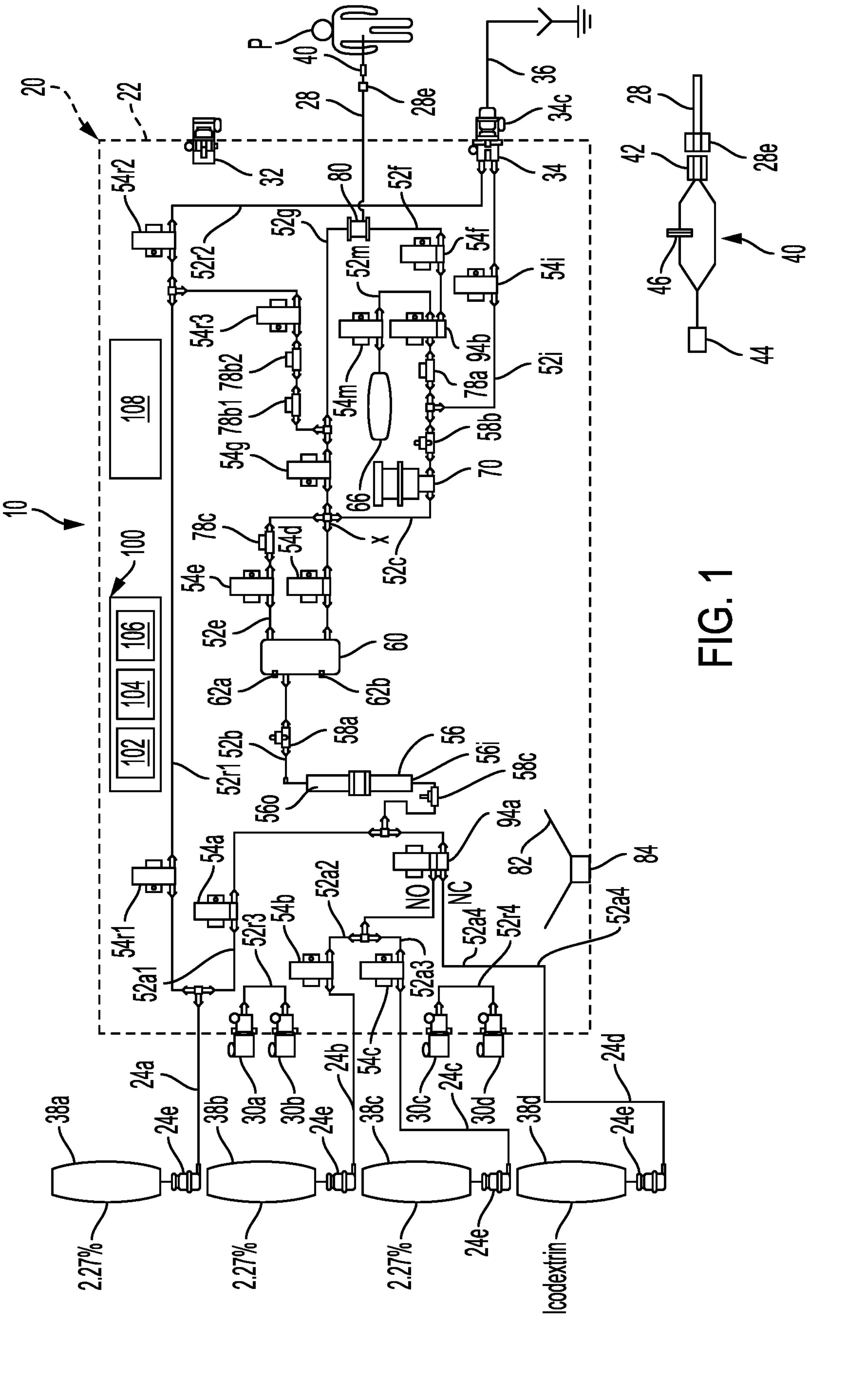
FIG. 1 is a fluid flow schematic of one embodiment for a medical fluid, e.g., PD fluid, system that is set for treatment.

Referring now to the drawings and in particular to FIG. 1, a medical system having the pump reversing heat disinfection of the present disclosure is illustrated via peritoneal dialysis ("PD") system 10. System 10 includes a PD machine or cycler 20 and a control unit 100 having one or more processor 102, one or more memory 104, video controller 106 and user interface 108. User interface 108 may alternatively or additionally be a remote user interface, e.g., via a tablet or smartphone. Control unit 100 may also include a transceiver and a wired or wireless connection to a network (not illustrated), e.g., the internet, for sending treatment data to and receiving prescription instructions/changes from a doctor's or clinician's server interfacing with a doctor's or clinician's computer. Control unit 100 in an embodiment controls all electrical fluid flow and heating components of system 10 and receives outputs from all sensors of system 10. System 10 in the illustrated embodiment includes durable and reusable components that contact fresh and used PD fluid, which necessitates that PD machine or cycler 20 be disinfected between treatments, e.g., via heat disinfection.

System 10 in FIG. 1 includes an inline resistive heater 56, reusable supply lines or tubes **52*a*1 to 52*a*4 and 52*b*, air trap 60 operating with respective upper and lower level sensors 62*a* and 62*b*, air trap valve 54*d*, vent valve 54*e* located along vent line 52*e*, reusable line or tubing 52*c*, PD fluid pump 70, temperature sensors 58*a* and 58*b* and possibly a third temperature sensor 58*c*, pressure sensors 78*a*, 78*b*1, 78*b*2 and 78*c*, reusable patient tubing or lines 52*f* and 52*g* having respective valves 54*f* and 54*g*, dual lumen patient line 28, a hose reel 80 for retracting patient line 28, reusable drain tubing or line 52*i* extending to drain line connector 34 and having a drain line valve 54*i*, and reusable recirculation tubing or lines 52*r*1 and 52*r*2 operating with respective disinfection valves 54*r*1 and 54*r*2. A third recirculation or disinfection tubing or line 52*r*3 extends between disinfection or PD fluid line connectors 30*a* and 30*b* for use during disinfection. A fourth recirculation or disinfection tubing or line 52*r*4 extends between disinfection connectors 30*c* and 30*d*** for use during disinfection.

System 10 further includes PD fluid containers or bags **38*a* to 38*c* (e.g., holding the same or different formulations of PD fluid), which connect to distal ends 24*e* of reusable PD fluid lines 24*a* to 24*c*, respectively. System 10*d* further includes a fourth PD fluid container or bag 38*d* that connects to a distal end 24*e* of reusable PD fluid line 24*d*. Fourth PD fluid container or bag 38*d* may hold the same or different type (e.g., icodextrin) of PD fluid than provided in PD fluid containers or bags 38*a* to 38*c*. Reusable PD fluid lines 24*a* to 24*d* extend in one embodiment through apertures (not illustrated) defined or provided by housing 22 of cycler 20**.

System 10 in the illustrated embodiment includes four disinfection or PD fluid line connectors **30*a* to 30*d* for connecting to distal ends 24*e* of reusable PD fluid lines 24*a* to 24*d*, respectively, during disinfection. System 10 also provides a patient line connector 32 that includes an internal lumen, e.g., a U-shaped lumen, which for disinfection directs fresh or used dialysis fluid from one PD fluid lumen of a connected distal end 28*e* of dual lumen patient line 28 into the other PD fluid lumen. Reusable supply tubing or lines 52*a*1 to 52*a*4 communicate with reusable supply lines 24*a* to 24*d*, respectively. Reusable supply tubing or lines 52*a*1 to 52*a*3 operate with valves 54*a* to 54*c*, respectively, to allow PD fluid from a desired PD fluid container or bag 38*a* to 38*c* to be pulled into cycler 20. Three-way valve 94*a* in the illustrated example allows for control unit 100 to select between (i) 2.27% (or other) glucose dialysis fluid from container or bag 38*b* or 38*c* and (ii) icodextrin from container or bag 38*d*. In the illustrated embodiment, icodextrin from container or bag 38*d* is connected to the normally closed port of three-way valve 94*a***.

System 10 is constructed in one embodiment such that drain line **52*i* during a patient fill is fluidly connected downstream from PD fluid pump 70. In this manner, if drain valve 54*i* fails or somehow leaks during the patient fill of patient P, fresh PD fluid is pushed down disposable drain line 36 instead of used PD fluid potentially being pulled into pump 70. Disposable drain line 36 is in one embodiment removed for disinfection, wherein drain line connector 34 is capped via a cap 34*c* to form a closed disinfection loop. PD fluid pump 70** may be an inherently accurate pump, such as a piston pump, or less accurate pump, such as a gear pump that operates in cooperation with a flowmeter (not illustrated) to control fresh and used PD fluid flowrate and volume.

System 10 may further include a leak detection pan 82 located at the bottom of housing 22 of cycler 20 and a corresponding leak detection sensor 84 outputting to control unit 100. In the illustrated example, system 10 is provided with an additional pressure sensor **78*c* located upstream of PD fluid pump 70, which allows for the measurement of the suction pressure of pump 70 to help control unit 100 more accurately determine pump volume. Additional pressure sensor 78*c* in the illustrated embodiment is located along vent line 52*e*, which may be filled with air or a mixture of air and PD fluid, but which should nevertheless be at the same negative pressure as PD fluid located within PD fluid line 52*c***.

System 10 in the example of FIG. 1 includes redundant pressure sensors **78*b*1 and 78*b*2, the output of one of which is used for pump control, as discussed herein, while the output of the other pressure sensor is a safety or watchdog output to make sure the control pressure sensor is reading accurately. Pressure sensors 78*b*1 and 78*b*2 are located along a line including a third recirculation valve 54*r*3. System 10 may further employ one or more cross, marked via an X in FIG. 1**, which may (i) reduce the overall amount and volume of the internal, reusable tubing, (ii) reduce the number of valves needed, and (iii) allow the portion of the fluid circuitry shared by both fresh and used PD fluid to be minimized.

System 10 in the example of FIG. 1 further includes a source of acid, such as a citric acid container or bag 66. Citric acid container or bag 66 is in selective fluid communication with second three-way valve **94*b* via a citric acid valve 54*m* located along a citric acid line 52*m*. Citric acid line 52*m* is connected in one embodiment to the normally closed port of second three-way valve 94*b*, so as to provide redundant valves between citric acid container or bag 66** and the PD fluid circuit during treatment. The redundant valves ensure that no citric (or other) acid reaches the treatment fluid lines during treatment. Citric (or other) acid is used instead during disinfection.

Control unit 100, in an embodiment, uses feedback from any one or more of pressure sensors **78*a* to 78*c* to enable PD machine 20 to deliver fresh, heated PD fluid to the patient at, for example, 14 kPa (2.0 psig) or higher. The pressure feedback is used to enable PD machine 20** to remove used PD fluid or effluent from the patient at, for example, between −5 kPa (−0.73 psig) and −15 kPa (−2.2 psig), such as −9 kPa (−1.3 psig) or higher (more negative). The pressure feedback may be used in a proportional, integral, derivative ("PID") pressure routine for pumping fresh and used PD fluid at a desired positive or negative pressure.

Inline resistive heater 56, under control of control unit 100, is capable of heating fresh PD fluid to body temperature, e.g., 37° C., for delivery to patient P at a desired flowrate. Control unit 100, in an embodiment, uses feedback from temperature sensor 58*a* in a PID temperature routine for pumping fresh PD fluid to patient P at a desired temperature. The control and operation of inline resistive heater 56 for heat disinfection is discussed in detail below.

FIG. 1 also illustrates that system 10 includes and uses a disposable filter set 40, which communicates fluidly with the fresh and used PD fluid lumens of dual lumen patient line 28. Disposable filter set 40 includes a disposable connector 42 that connects to a distal end 28*e* of reusable patient line 28. Disposable filter set 40 also includes a connector 44 that connects to the patient's transfer set. Disposable filter set 40 further includes a sterilizing grade filter membrane 46 that further filters fresh PD fluid. Disposable filter set 40 is provided in one embodiment as a last chance filter for PD machine 20, which has been heat disinfected between treatments. Any pathogens that may remain after disinfection, albeit unlikely, are filtered from the PD fluid via the sterilizing grade filter membrane 46 of disposable filter set 40.

FIG. 1 illustrates system 10 setup for treatment with PD fluid containers or bags 38*a* to 38*d* connected via reusable, flexible PD fluid lines 24*a* to 24*d*, respectively. Dual lumen patient line 28 is connected to patient P via disposable filter set 40. Disposable drain line 36 is connected to drain line connector 34. In FIG. 1, PD machine or cycler 20 of system 10 is configured to perform multiple patient drains, patient fills, patient dwells, and a priming procedure, as part of or in preparation for treatment.

Figure 2:
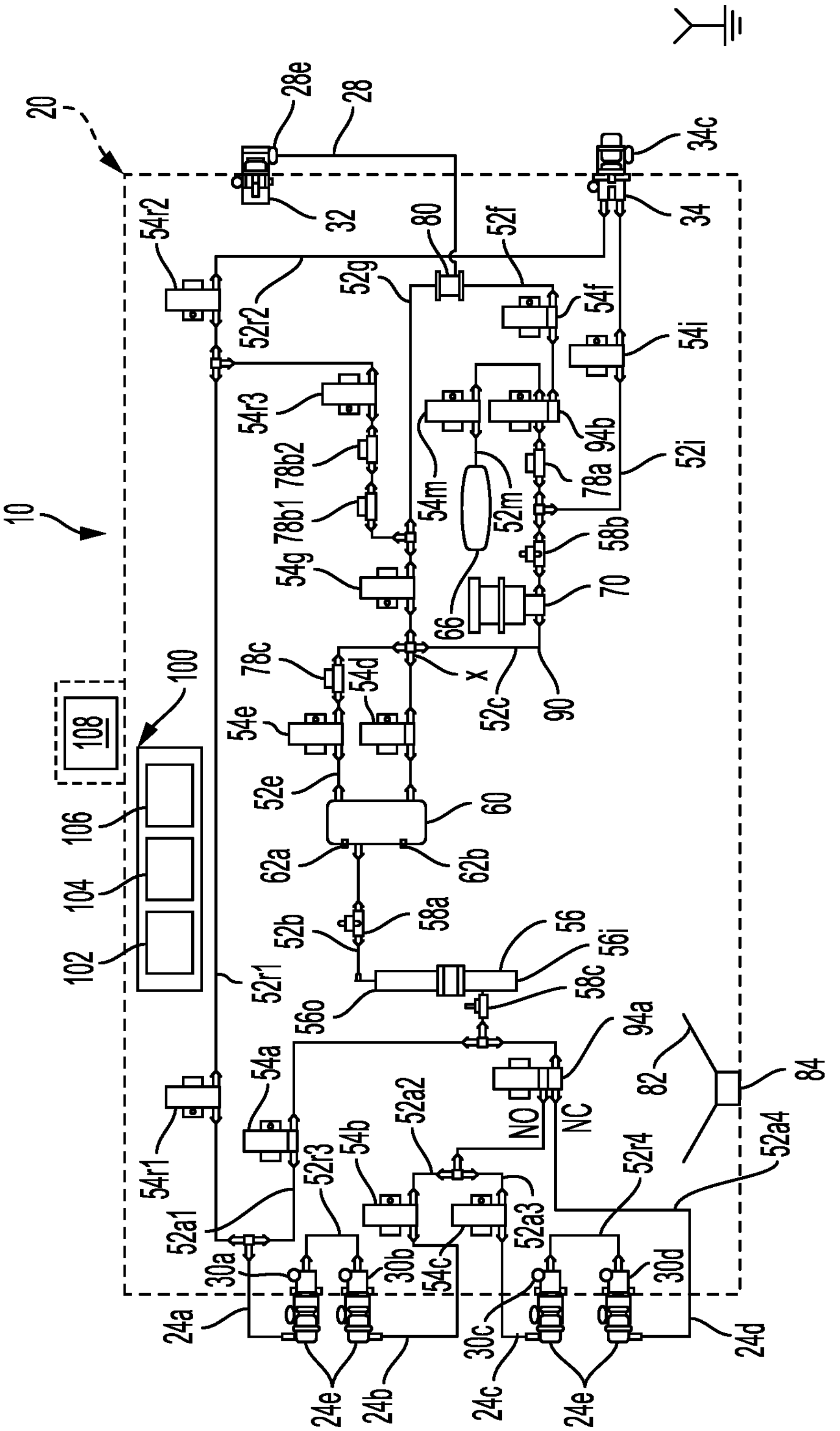
FIG. 2 is a fluid flow schematic of one embodiment for a medical fluid, e.g., PD fluid, system of FIG. 1, which has been rearranged for disinfection.

FIG. 2 illustrates system 10 in a disinfection mode. PD fluid containers or bags 38*a* to 38*d* are removed and flexible PD fluid lines 24*a* to 24*d* are plugged instead in a sealed manner into disinfection or PD fluid line connectors 30*a* to 30*d*, respectively. Reusable dual lumen patient line 28 is disconnected from disposable filter set 40 (which is discarded), and distal end 28*e* of dual lumen patient line 28 is plugged sealingly into patient line connector 32. Disposable drain line 36 is removed from drain line connector 34 and discarded. Drain line connector 34 is capped via cap 34*c* to form a closed disinfection loop 90. PD machine or cycler 20 of system 10 in FIG. 2 is configured to perform a disinfection sequence, e.g., a heat disinfection sequence in which fresh PD fluid is heated via inline heater 56 to a disinfection temperature of, e.g., 75° C. or greater. PD fluid pump 70 circulates the heated PD fluid closed disinfection loop 90 for an amount of time needed to properly disinfect the fluid components and lines of the disinfection loop.

Pump Reversing Heat Disinfection

In one embodiment, control unit 100 causes PD fluid pump 70 and the valves of system 10 at the beginning of a heat disinfection sequence to move the heated PD fluid in a normal treatment direction, e.g., from left to right, across PD fluid pump 70 in FIG. 2. Heated PD fluid may split between fresh patient tubing or line 52*f* and drain tubing or line 52*i*. Heated PD fluid flow splitting through fresh patient tubing or line 52*f* proceeds to flow through: the fresh PD lumen of dual lumen patient line 28, the used PD lumen of dual lumen patient line 28, used patient tubing or line 52*g*, and tubing or line 52*c*, back to PD fluid pump 70. Heated PD fluid flow splitting through fresh patient tubing or line 52*f* also further splits into the line including pressure sensors 78*b*1 and 78*b*2 and third recirculation valve 54*r*3 after which it joins the heated PD fluid flow through recirculation line 52*r*1.

Heated PD fluid flow splitting through drain tubing or line 52*i* proceeds to flow through drain line connector 34, recirculation tubing or line 52*r*2, recirculation tubing or line 52*r*1, reusable flexible PD fluid lines 24*a* to 24*d*, tubing or lines 52*a*1 to 52*a*4, recirculation tubing or lines 52*r*3 and 52*r*4, back to the inlet of inline heater 56. The length of internal reusable tubing and reusable flexible PD fluid lines 24*a* to 24*d* between the outlet of inline heater 56 and the inlet of inline heater 56 may be ten meters or more. Heat loss will occur over the length of the lines. A potential problem may accordingly occur in which while the PD fluid leaving inline heater 56 is at a temperature sufficient to produce a desired amount of disinfection, the temperature of PD fluid returning to and entering inline heater 56 is below what is considered a threshold minimum disinfection temperature.

Figure 3:
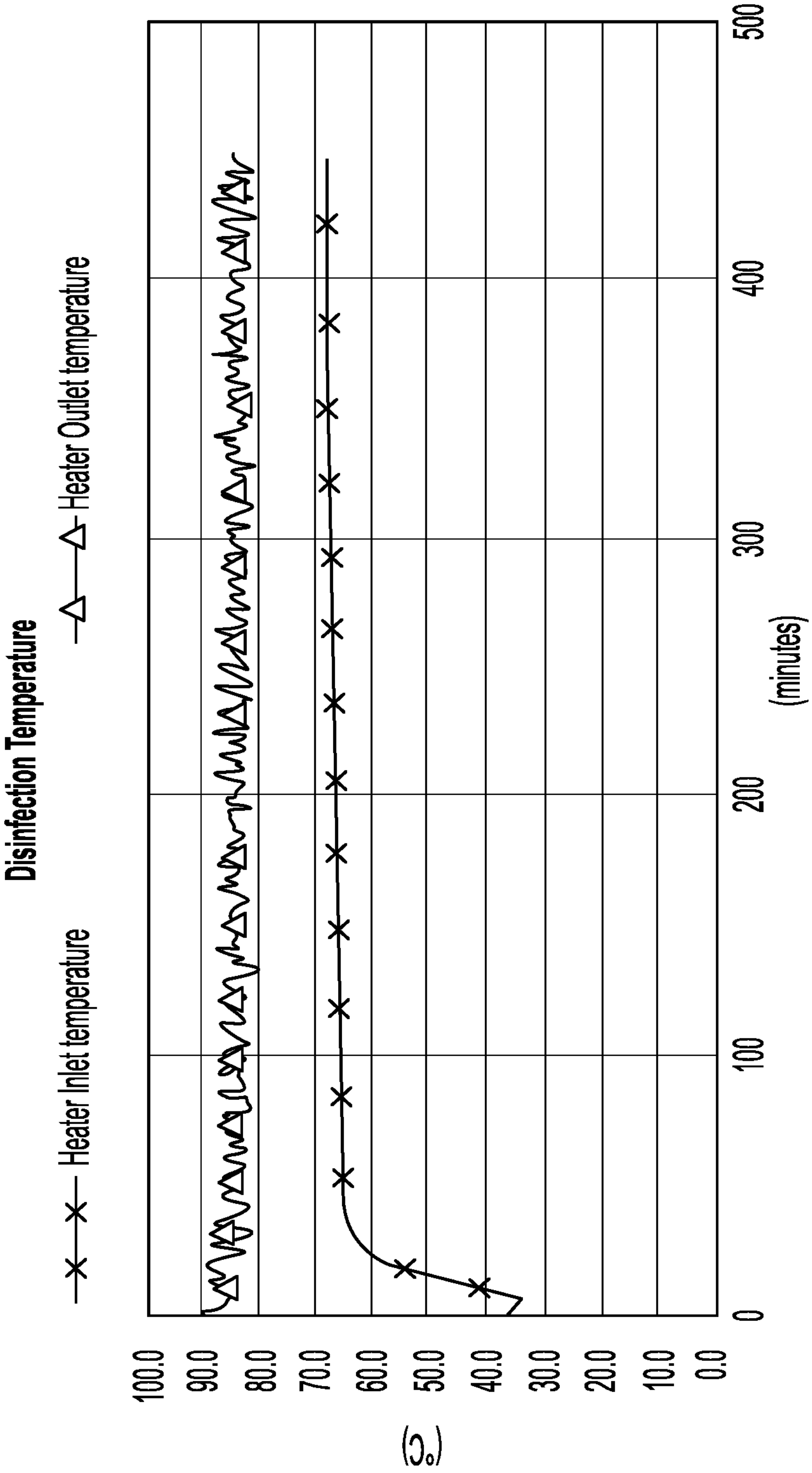
FIG. 3 includes plots showing inline heater inlet temperature versus inline heater outlet temperature when the pump reversing disinfection of the present disclosure is not used or employed.

In one example, control unit 100 under feedback from temperature sensor 58*a* energizes inline heater 56 such that PD fluid exiting the heater is at or about 85° C. 85° C. (185° F.) is in one embodiment be a desired output disinfection temperature because it is above a recommended minimum disinfection temperature of, e.g., 75° C. (167° F.) and it is below a temperate in which the PD fluid may start to boil. If the temperature of PD fluid reaching heater inlet 56*i* of inline heater 56 falls below the recommended minimum disinfection temperature of, e.g., 65° C. (149° F.) to 95° C. (203° F.), such as 75° C. (167° F.), then corrective action needs to be taken. FIG. 3 includes plots illustrating the temperature at heater inlet 56*i* versus the temperature at heater outlet 56*o* without the pump reversing of the present disclosure. Here, the temperature of outlet 56*o* of heater 56 varies between 80° C. (176° F.) and 90° C. (194° F.) and remains above the recommended minimum disinfection temperature of, e.g., 75° C. (167° F.), however, the temperature of inlet 56*i* of heater 56 approaches but remains below 70° C. (158° F.). The temperature of inlet 56*i* of heater 56 accordingly likely falls below the recommended minimum disinfection temperature of, e.g., 75° C. (167° F.). Time varies in minutes in the illustrated embodiment.

Corrective measures to raise the temperature of inlet 56*i* of heater 56 illustrated in FIG. 3 may include raising the heater outlet temperature, increasing disinfection time or some combination of both. But raising the heater outlet temperature above 85° C. runs the risk of beginning to boil the PD fluid, while increasing disinfection time increases component wear. System 10 and associated methodology instead solve the potential low temperature problem by programing control unit 100 to automatically reverse the pumping direction of PD fluid pump 70 one or more time during the disinfection sequence so that freshly heated PD fluid, e.g., at 85° C., is outputted from what is typically the heater inlet 56*i* of inline heater 56. Inline heater 56 is in one embodiment bidirectional, such that PD fluid flowing in either direction from inlet 56*i* to outlet 56*o*, or from outlet 56*o* to inlet 56*i* may be heated to a desired temperature under the control of control unit 100. It may be possible to use an inline heater 56 that is not bidirectional. Here, control unit 100 may cause PD fluid to be heated in the normal direction for a desired number of pump strokes and to a desired and controlled temperature, after which PD fluid pump 70 is caused to pump in the reverse direction for the same desired number of pump strokes to push the freshly heated PD fluid out heater inlet 56*i*. While pumping in the reverse direction, inline heater 56 may or may not be powered.

Reversing the pumping direction of PD fluid pump 70 one or more time during the disinfection sequence causes the freshly heated PD fluid, e.g., to 85° C., to be distributed more evenly. Here, the hotter freshly heated PD fluid mixes with the cooler PD fluid returning to inline heater 56, bringing the mixed PD fluid temperature to above the recommended minimum disinfection temperature of, e.g., 75° C. The more even distribution of freshly heated PD fluid helps to eliminate pockets of closed disinfection loop 90 that may fall below the recommended minimum disinfection temperature. The more even distribution of freshly heated PD fluid also helps to reduce the amount of time needed for the disinfection sequence. For example, the time for the disinfection sequence may be cut roughly in half from two hours to one hour using the pump reversing heated PD fluid disinfection of the present disclosure.

Figure 4:
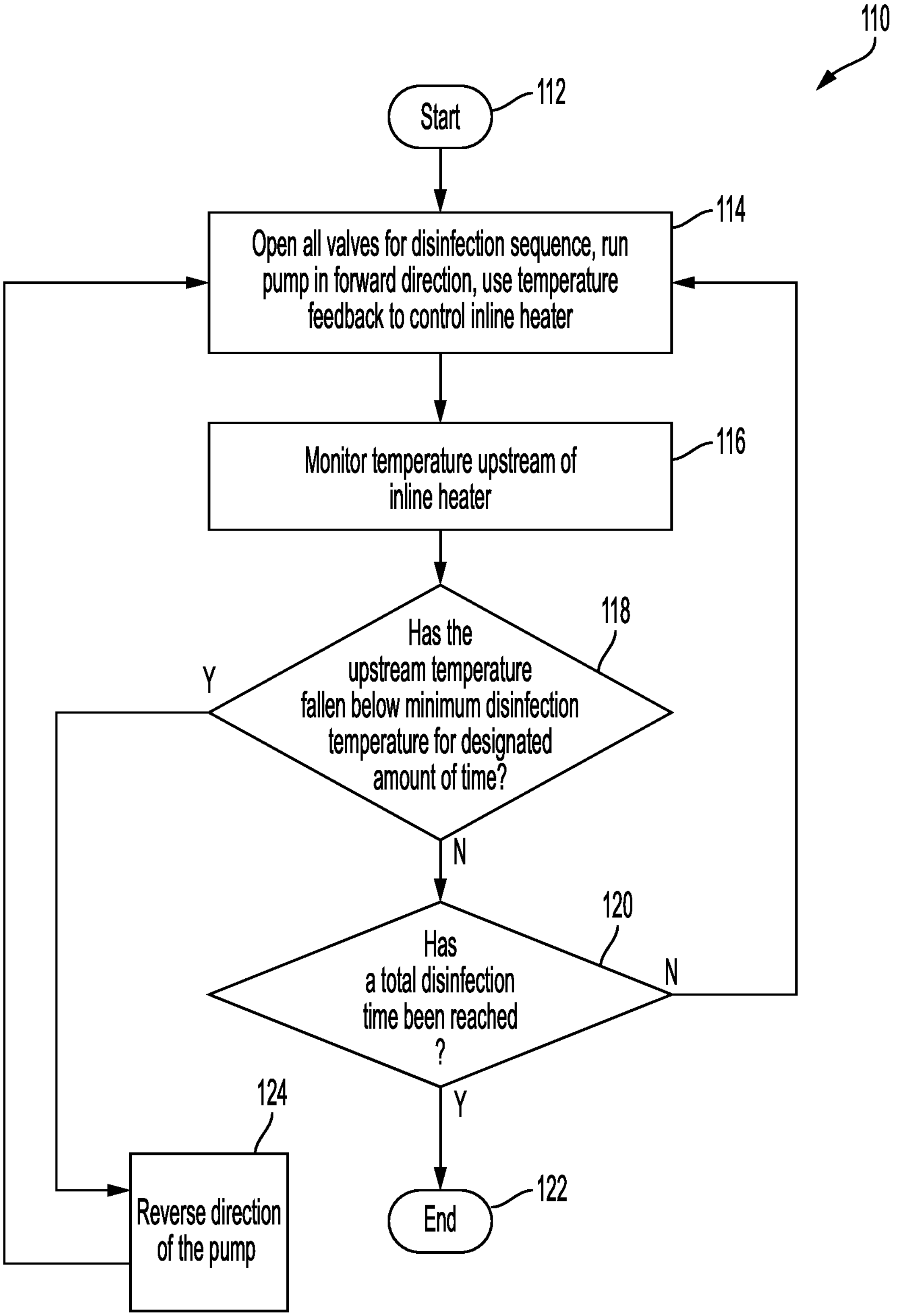
FIG. 4 is a process flow diagram illustrating one embodiment for reversing the flow of heated PD fluid during a disinfection sequence of the present disclosure.

FIG. 4 shows one method 110, which may be implemented in control unit 100 for controlling the pump reversing during heat disinfection of the present disclosure. At oval 112, method 110 begins. At block 114, control unit 100 opens all two-way valves associated with disinfection loop 90 and runs PD fluid pump 70 in a forward treatment direction (left to right through pump 70 in FIGS. 1 and 2), which is also considered to be the normal disinfection sequence direction. At block 114, control unit 100 also uses feedback from temperature sensor 58*a* and a heating algorithm, such as a proportional, integral, derivative ("PID") heating algorithm, to control inline heater 56 to output heated PD fluid at heater outlet 56*o* at a desired disinfection temperature, such as 85° C.

At block 116, control unit 100 monitors the output of temperature sensor 58*c*, which is the temperature of heated PD fluid reentering inline heater 56 at heater inlet 56*i*. At diamond 118, control unit 100 determines whether the temperature of the PD fluid reentering inline heater 56 at heater inlet 56*i*, as indicated by temperature sensor 58*c*, has fallen below a recommended minimum disinfection temperature of, e.g. 75° C., for a threshold or designated amount of time, such as sixty seconds. Including a threshold amount of time in the query at diamond 118 allows for the PD fluid temperature at heater inlet 56*i* to fall below the recommended minimum disinfection temperature for short periods of time, or inadvertently, without overreacting to the temporary temperature drop. It is contemplated to optimize the threshold amount of time to allow for a looser version of method 110, e.g., longer than one minute, or for a tighter version of method 110, e.g., five to sixty seconds.

If the temperature of the PD fluid reentering inline heater 56 at heater inlet 56*i* has not fallen below the recommended minimum disinfection temperature for the threshold amount of time, as determined at diamond 118, then at diamond 120, control unit 100 determines whether a total disinfection sequence time has been reached. Proper disinfection of disinfection loop 90 involves the movement of PD fluid heated at or above the recommended minimum disinfection temperature through disinfection loop 90 for a specified period of time, e.g., two hours. Once the total or specified disinfection time is reached, as determined at diamond 120, the disinfection sequence is completed and method 110 ends at oval 122.

If at diamond 120, if the total or specified disinfection time has not been reached, method 110 returns to block 114 as illustrated in FIG. 4. The loop just described between block 114 and diamond 120 is repeated until either the total or specified disinfection time has been reached (at diamond 120) or the temperature of the PD fluid reentering inline heater 56 at heater inlet 56*i* has fallen below the recommended minimum disinfection temperature for the threshold amount of time (at block 118).

At block 118, when the temperature of the PD fluid reentering inline heater 56 at heater inlet 56*i* has fallen below the recommended minimum disinfection temperature for the threshold amount of time, control unit 100 at block 124 causes PD fluid pump 70 to reverse and pump in the opposite direction (right to left in FIGS. 1 and 2). Control unit 100 also sequences any of the valves of disinfection loop 90 as needed, e.g., sequences three-way valve 94*a*. It is contemplated for control unit 100 to control the amount or time that the pumping of PD fluid pump 70 is reversed in a plurality of different ways. In one way, control unit 100 causes PD fluid pump 70 to pump in the reverse direction for a number of pump strokes, e.g., one-hundred pump strokes. In a second way, control unit 100 causes PD fluid pump 70 to pump in the reverse direction until a certain temperature is reached at temperature sensor 58*c*, e.g., 85° C. (commanded output of heater 56), wherein temperature sensor 58*c* is the downstream temperature sensor during reverse pumping. In a third way, control unit 100 causes PD fluid pump 70 to pump in the reverse direction until a certain temperature is reached at temperature sensor 58*c*, e.g., 85° C., after which a preset number of additional pump strokes are performed in the reverse pumping direction.

When the reversed pumping of PD fluid pump 70 is completed via any of the ways discussed above, method 110 returns to block 114 as illustrated in FIG. 4. As discussed in connection with diamond 118 and block 124, temperature sensor 58*c* located just upstream of heater inlet 56*i* in the normal pumping direction is used as part of the trigger for beginning the pump reversing (diamond 118) and possibly in determining how long the pump reversing is performed (block 124). The output of temperature sensor 58*c* is also used as feedback to control unit 100 for controlling the powering of inline heater 56 while the pumping of PD fluid pump 70 is reversed, so that a maximum temperature, e.g., 85° C. is not exceeded.

Figure 5:
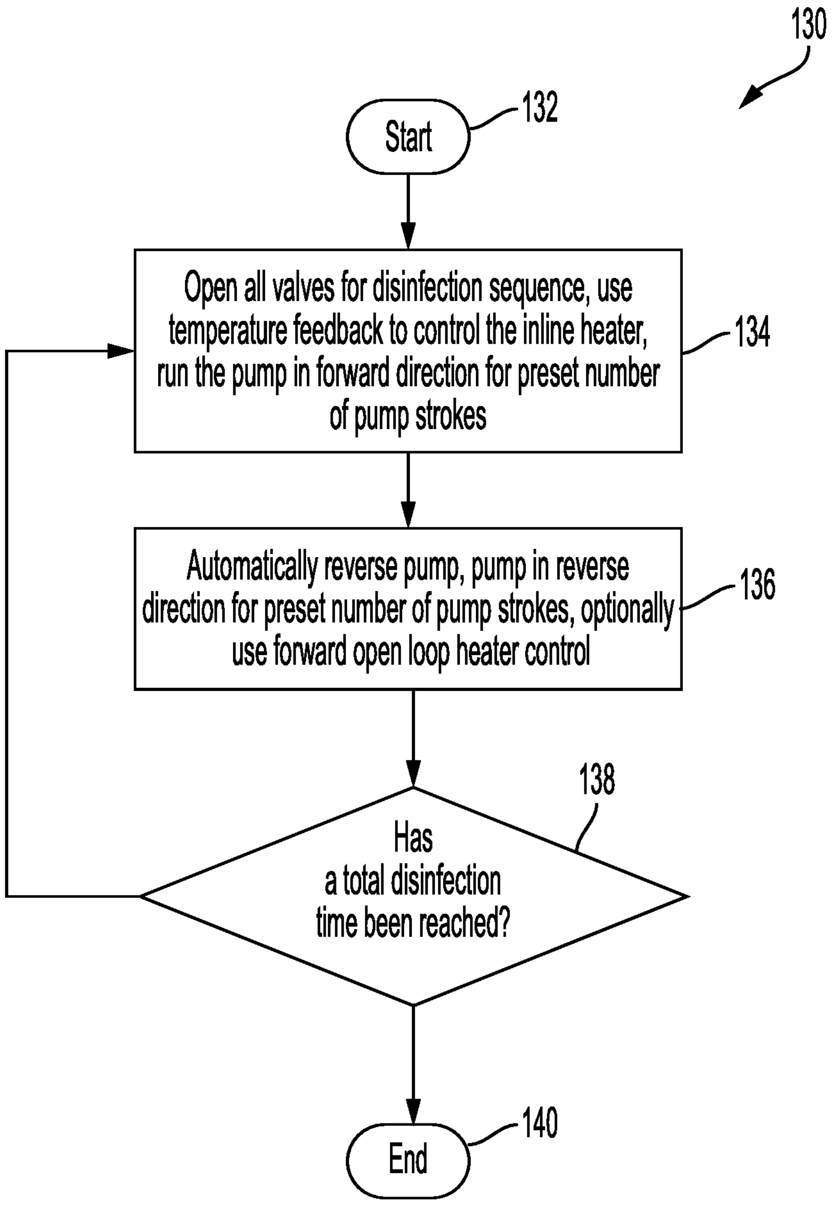
FIG. 5 is a process flow diagram illustrating another embodiment for reversing the flow of heated PD fluid during a disinfection sequence of the present disclosure.

FIG. 5 illustrates an alternative method 130 in which temperature sensor 58*c* located just upstream of heater inlet 56*i* may not be needed, which is advantageous for reducing cost, eliminating a sensor that may need calibration from time to time, and eliminating a part that may need to be replaced. At block 132, method 130 begins. At block 134, control unit 100 opens all two-way valves associated with disinfection loop 90. At block 134, control unit 100 also uses feedback from temperature sensor 58*a* and a heating algorithm, such as a proportional, integral, derivative ("PID") heating algorithm, to control inline heater 56 to output heated PD fluid at heater outlet 56*o* at a desired disinfection temperature, such as 85° C. At block 134, control unit 100 causes PD fluid pump 70 to pump in the normal treatment (forward) direction (left to right through pump 70 in FIGS. 1 and 2) for a preset number of pump strokes, e.g., 100 pump strokes.

At block 136, after the preset number of pump strokes in the treatment direction have been completed, control unit 100 causes PD fluid pump 70 to automatically reverse and pump in the opposite direction (right to left in FIGS. 1 and 2). Control unit 100 also sequences any of the valves of disinfection loop 90 as needed, e.g., sequences three-way valve 94*a*. In one embodiment, control unit 100 causes PD fluid pump 70 to pump in the reverse direction for a preset number of pump strokes, e.g., one-hundred pump strokes. As discussed below, control unit 100 may in one embodiment use forward open loop heater control during the pump reversing of method 130, which does not require the use of temperature sensor 58*c* (but closed loop control using temperature sensor 58*c* could be performed alternatively).

At diamond 138, after the preset number of pump strokes in the reverse direction have been completed, control unit 100 determines whether a total disinfection sequence time has been reached. Proper disinfection of disinfection loop 90 for method 130 again involves the movement of PD fluid heated at or above the recommended minimum disinfection temperature through disinfection loop 90 for a specified period of time. If the total or specified disinfection time has not been is reached, as determined at diamond 138, method 130 returns to block 134. Once the total or specified disinfection time is reached, as determined at diamond 138, the disinfection sequence is completed and method 130 ends at oval 140.

Figure 6:
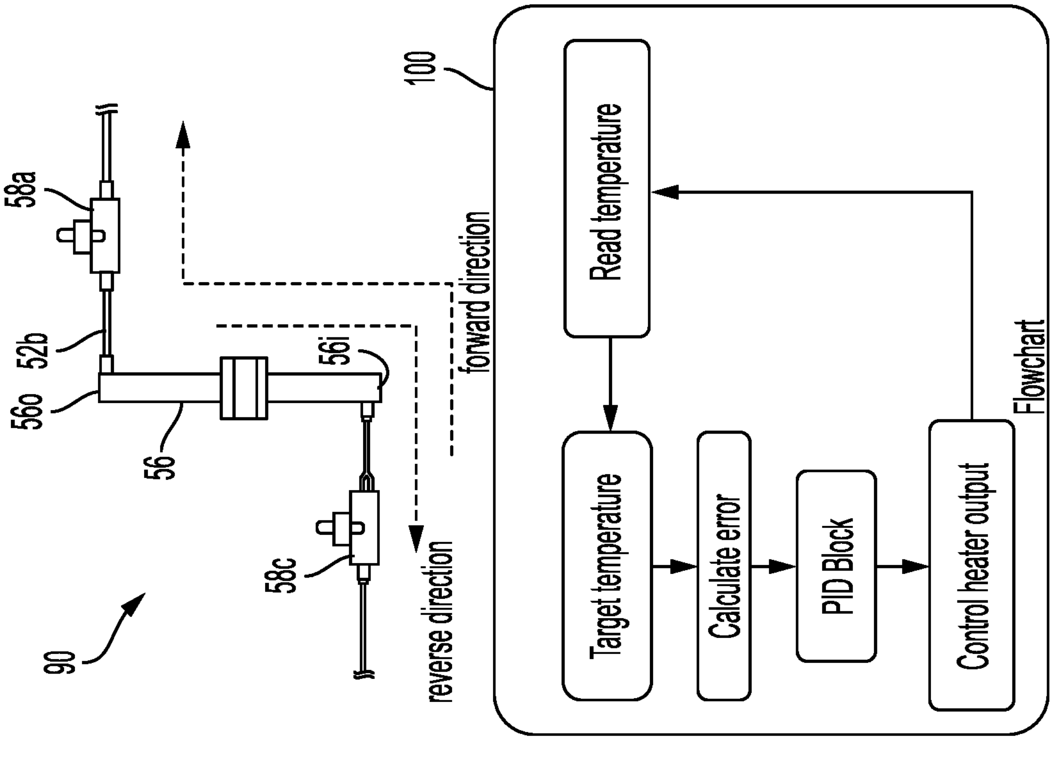
FIG. 6 illustrates a partial fluid path showing an inline heater and temperature sensors for closed loop control, which may be employed for both forward and reverse PD fluid disinfection flow.

FIG. 6 illustrates one embodiment for using a downstream pressure sensor for closed loop control, which may be employed in method 110 for both forward and reverse heated PD fluid disinfection flow and in method 130 for forward heated PD fluid disinfection flow. FIG. 6 illustrates a portion of disinfection loop 90 having inline heater 56, temperature sensor 58*a* outputting to control unit 100 and temperature sensor 58*c* outputting to control unit 100. In the forward direction, the output from temperature sensor 58*a* is used for feedback control. In reverse direction, the output from temperature sensor 58*c* is used for feedback control.

FIG. 5 illustrates that for closed loop control, control unit 100 reads the temperature from the pertinent temperature sensor 58*a*, 58*c*. Control unit 100 also stores a target temperature, e.g., 85° C. Control unit 100 calculates an error between the commanded or target temperature and the temperature read from the pertinent temperature sensor 58*a*, 58*c*. Control unit 100 then inputs the calculated error into the heating algorithm, e.g., PID heating algorithm. An output from the heating algorithm is used by control unit 100 to determine how much power to deliver to inline heater. The cycle just described is repeated at some processing frequency.

It should be appreciated that for both methods 110 and 130, closed loop control in the forward direction should very quickly produce a temperature reading at temperature sensor 58*a* in the range of the commanded temperature, e.g., 85° C. For method 100, which triggers the reverse flow when temperature sensor 58*c* senses a low temperature for a certain period of time as discussed above, that same temperature sensor 58*c*, which is then used for closed loop control, will initially read a lower temperature corresponding to a mixture of hot PD fluid exiting inline heater 56 in the reverse direction and cooler PD fluid residing just upstream from heater inlet 56*i*. Here, a period of time will occur before temperature sensor 58*c* begins to read temperatures in the range of the commanded temperature, e.g., 85° C.

Figure 7:
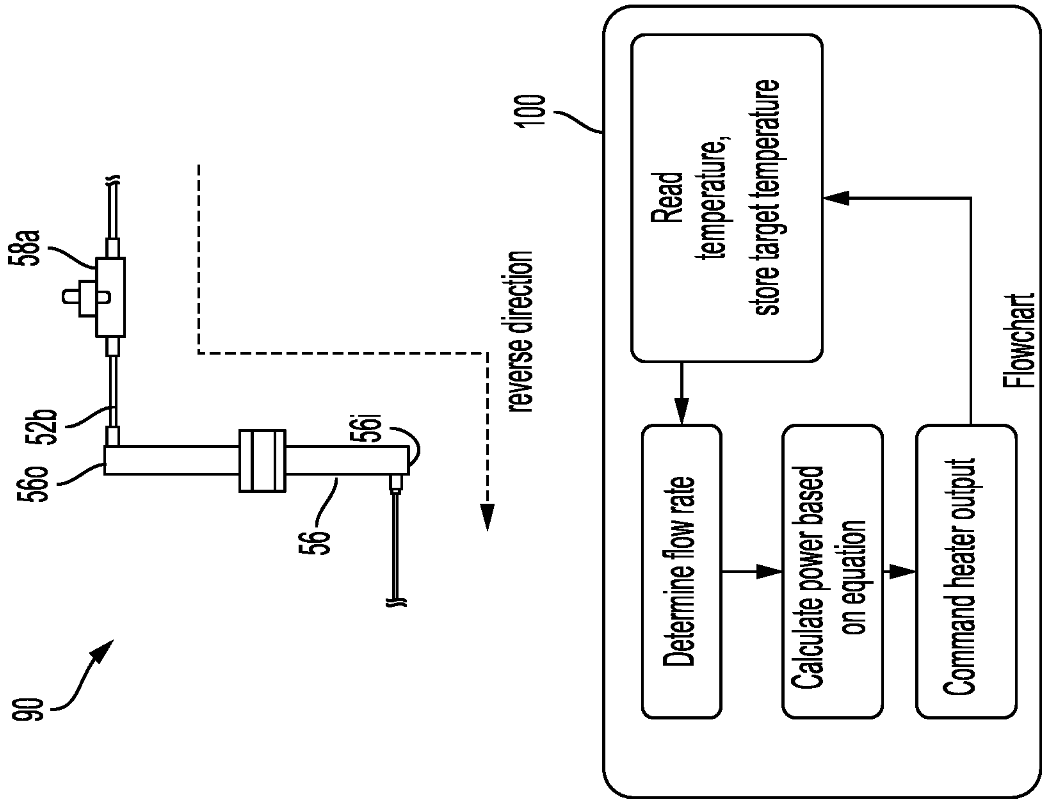
FIG. 7 illustrates a partial fluid path showing an inline heater and an upstream temperature sensor for an open loop forward heating control algorithm used during reverse PD fluid disinfection flow.

FIG. 7 illustrates an alternative way to control inline heater 56 during reverse PD fluid flow, which involves a forward open loop control, and which does not require temperature sensor 58*c* (missing in FIG. 7). The forward open loop heater control is accordingly suitable for the reverse PD fluid flow of method 130. The forward open loop heater control of FIG. 7 used during the reverse PD fluid flow of method 130 uses an output from temperature sensor 58*a* to control unit 100. It should be appreciated that during reverse PD fluid flow, temperature sensor 58*a* is located upstream of heater outlet 56*o* of inline heater 56.

FIG. 6 illustrates that for open loop control, control unit 100 reads the temperature from temperature sensor 58*a* and also stores a target temperature, e.g., 85° C. Control unit 100 also determines (calculates or measures) a current PD fluid flowrate. If a piston pump is used as PD fluid pump 70 and no flowmeter is provided, control unit 100 calculates the current flowrate by accumulating known volume pump strokes pumped by PD fluid pump 70 and dividing the accumulated volume by an amount of time needed to make the pump strokes accumulated. If instead a separate flowmeter is provided (not illustrated in FIGS. 1 and 2), then control unit 100 measures the flowrate by reading an output from the flowmeter.

At FIG. 7, control unit 100 inputs the temperature from temperature sensor 58*a* and the determined flowrate into a feed forward heater algorithm. An output from the feed forward heater algorithm (or derivative or correlation thereof) is used by control unit 100 to determine how much power to deliver to inline heater. The cycle just described is repeated at some processing frequency. In one example, the feed forward heater algorithm may be:

$$\text{required heater output power} = (\text{target temperature} - \text{inlet temperature}) \times PD \text{ fluid flowrate} \times \text{specific heater of water}$$

In an example in which the inlet temperature read by temperature sensor 58*a* is 70° C., the target temperature is 85° C., the determined flowrate is 300 ml/min (5 ml/second), and the specific heat of water is 4.184 (Jouls/grams×° K), then the needed output power is (85-70)×5×4.184, which equals 313.8 Watts of heating power. In an embodiment, memory 104 of control unit stores a lookup table for inline heater 56, which correlates how much current or heater inlet power is needed to achieve 313.8 Watts of heating power (or closest power stored).

Figure 8:
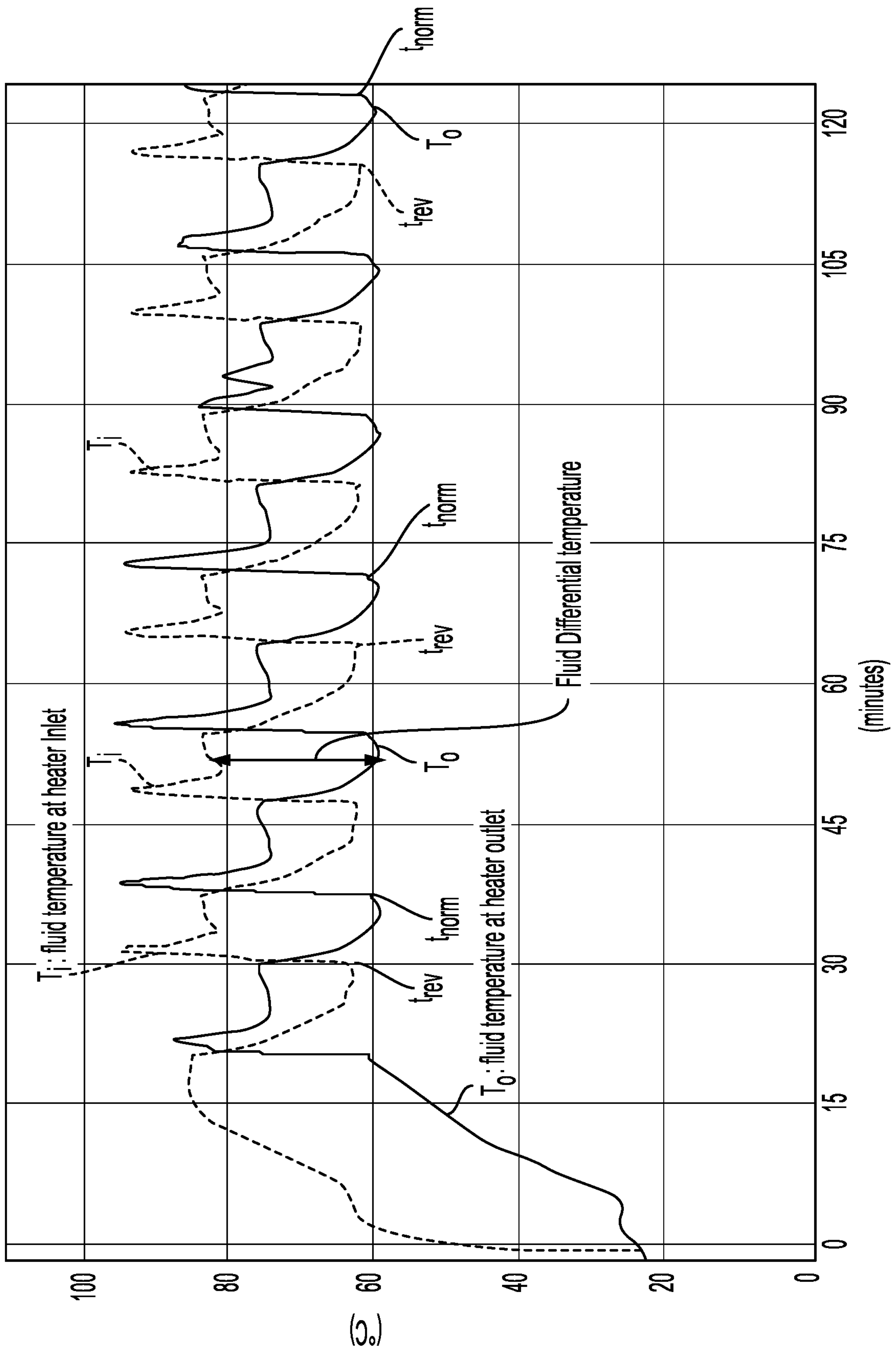
FIG. 8 includes plots showing inline heater inlet temperature and inline heater outlet temperature over time, and illustrating the effects of the pump reversing disinfection of the present disclosure.

FIG. 8 illustrates two temperature plots Ti and To over time, which are of the temperature at inlet 56*i* of inline heater 56 and the temperature at outlet 56*o* of inline heater 56, respectively. The reversing of PD fluid pump 70 during disinfection caused by control unit 100 occurs, e.g., at times $t_{rev}$, where a sharp increase in temperature occurs at inlet 56*i* of heater 56. The stopping of the reversing of PD fluid pump 70 during disinfection caused by control unit 100 to instead pump again in the normal direction occurs, e.g., at times $t_{norm}$, where a sharp increase in temperature occurs at outlet 56*o* of heater 56. It should be appreciated that while temperatures in both temperature plots Ti and To are shown falling to about 60° C. (140° F.), which is likely below the minimum disinfection temperature, the power (or duty cycle) to heater 56 may be increased such that the minimum temperatures for temperature plots Ti and To do not, or do not significantly, fall below minimum disinfection temperature, e.g., 75° C. (167° F.). Time varies in minutes in the illustrated embodiment. The importance of FIG. 8 is to show that the pump reversing does have a significant and immediate impact of the temperature at inlet 56*i* of inline heater 56.

It should be understood that various changes and modifications to the presently preferred embodiments described herein will be apparent to those skilled in the art. It is therefore intended that such changes and modifications be covered by the appended claims.

The invention is claimed as follows:

1. A peritoneal dialysis ("PD") system comprising:

a housing;

a PD fluid pump housed by the housing;

an inline heater in fluid communication with the PD fluid pump;

a temperature sensor; and a control unit, the PD fluid pump and the inline heater being under control of the control unit, the control unit configured to:

receive a temperature signal from the temperature sensor, and perform a heat disinfection sequence in which the control unit causes the PD fluid pump to pump disinfection fluid in a forward direction, while the inline heater heats the disinfection fluid, and in a reverse direction after the temperature signal indicates that a temperature of the disinfection fluid has fallen to or has fallen below a minimum disinfection temperature.

2. The PD system of claim 1, wherein the control unit is configured to cause the PD fluid pump to pump the disinfection fluid in the reverse direction after the temperature signal indicates, over a designated amount of time, that the temperature of the disinfection fluid has fallen to or has fallen below the minimum disinfection temperature.

3. The PD system of claim 1, wherein the temperature sensor is located upstream of the inline heater when the PD fluid pump is pumping the disinfection fluid in the forward direction.

4. The PD system of claim 1, wherein the temperature signal is used as closed loop feedback to the control unit for controlling the inline heater when the PD fluid pump is pumping the disinfection fluid in the reverse direction.

5. The PD system of claim 1, wherein the temperature sensor is a first temperature sensor, and which includes a second temperature sensor located downstream of the inline heater when the PD fluid pump is pumping the disinfection fluid in the forward direction, and wherein a temperature signal from the second temperature sensor is used as closed loop feedback to the control unit for controlling the inline heater when the PD fluid pump is pumping the disinfection fluid in the forward direction.

6. The PD system of claim 5, wherein the inline heater is controlled such that a temperature of the disinfection fluid exiting the inline heater is about 85° C.

7. The PD system of claim 1, wherein the control unit is configured to cause the PD fluid pump to pump the disinfection fluid in the reverse direction for a number of pump strokes.

8. The PD system of claim 1, wherein the control unit is configured to cause the PD fluid pump to pump the disinfection fluid in the reverse direction until a certain temperature is reached, as indicated by the temperature sensor.

9. The PD system of claim 1, wherein the control unit is configured to cause the PD fluid pump to pump the disinfection fluid in the reverse direction until a certain temperature is reached, as indicated by the temperature sensor, followed by a number of pump strokes in the reverse direction.

10. The PD system of claim 1, wherein the heat disinfection sequence is performed using a disinfection loop including:

a reusable patient line extending from the housing, the reusable patient line including a distal end configured to be connected to a patient line connector provided by the housing; and at least one reusable PD fluid line extending from the housing, the at least one reusable PD fluid line including a distal end configured to be connected to a PD fluid line connector provided by the housing.

11. The PD system of claim 1, wherein at least one of (i) the minimum disinfection temperature is from 65° C. (149° F.) to 95° C. (203° F.) or (ii) the disinfection fluid is PD fluid.

12. A peritoneal dialysis ("PD") system comprising:

a housing;

a PD fluid pump housed by the housing;

an inline heater in fluid communication with the PD fluid pump;

a temperature sensor; and a control unit, the PD fluid pump and the inline heater being under control of the control unit, the control unit configured to:

receive a temperature signal from the temperature sensor, and perform a heat disinfection sequence in which the control unit causes the PD fluid pump to pump disinfection fluid in a forward direction, while the inline heater heats the disinfection fluid, and in a reverse direction in which the control unit controls the inline heater using a feed forward algorithm that takes into account the temperature signal and a flowrate of the disinfection fluid.

13. The PD system of claim 12, wherein the temperature signal provides a heater inlet temperature, and wherein the feed forward algorithm subtracts the heater inlet temperature from a target temperature.

14. The PD system of claim 12, wherein the flowrate of the disinfection fluid is calculated by the control unit by accumulating known pump volumes pumped by the PD fluid pump.

15. The PD system of claim 12, which includes a flowmeter in fluid communication with the PD fluid pump, wherein the flowrate of the disinfection fluid is measured by the flowmeter.

16. The PD system of claim 12, wherein the feed forward algorithm is structured to calculate an output power=(a target temperature-an inlet temperature obtained from the temperature signal)×(the disinfection fluid flowrate)×(the specific heat of water).

17. The PD system of claim 16, wherein the target temperature is 85° C.

18. The PD system of claim 12, wherein the temperature sensor is located downstream of the inline heater when the PD fluid pump is pumping the disinfection fluid in the forward direction, and wherein the temperature signal is used as closed loop feedback to the control unit for controlling the inline heater when the PD fluid pump is pumping the disinfection fluid in the forward direction.

19. The PD system of claim 12, wherein the control unit is configured to cause (i) the PD fluid pump to pump the disinfection fluid in the forward direction for a number of pump strokes, and (ii) the PD fluid pump to automatically reverse and pump the disinfection fluid in the reverse direction for a number of pump strokes.

20. The PD system of claim 19, wherein the control unit is further configured to repeat (i) and (ii) until a total disinfection time is reached.

* * * * *